United States Patent [19]

Fujiwara et al.

[11] Patent Number: 5,036,697
[45] Date of Patent: Aug. 6, 1991

[54] APPARATUS FOR DETECTING GAS-LIQUID RATIO OF A FLUID

[75] Inventors: Kenichi Fujiwara, Kariya; Kazutoshi Nishizawa, Toyoake; Kenji Yamada, Chiryu, all of Japan

[73] Assignee: Nippondenso Co., Ltd., Kariya, Japan

[21] Appl. No.: 502,674

[22] Filed: Apr. 2, 1990

[51] Int. Cl.$^5$ .............................................. G01N 7/14
[52] U.S. Cl. ........................................ 73/19.1; 62/126
[58] Field of Search ................... 73/19.01, 19.1, 19.12, 73/53, 61 R, 61.3, 64.2; 340/608; 62/126, 127, 129

[56] References Cited

U.S. PATENT DOCUMENTS

| | | | |
|---|---|---|---|
| 4,167,858 | 9/1979 | Kojima et al. | 62/126 |
| 4,344,293 | 8/1982 | Fujiwara et al. | 62/126 |
| 4,375,751 | 3/1983 | McCord | 62/126 |
| 4,614,087 | 9/1986 | Nadamoto et al. | 62/126 |
| 4,677,830 | 7/1987 | Sumikawa et al. | 62/126 |
| 4,763,514 | 8/1988 | Naito et al. | 73/19.11 |

FOREIGN PATENT DOCUMENTS 48-69148 9/1973 Japan .
61-14430 4/1986 Japan .

*Primary Examiner*—Hezron E. Williams
*Assistant Examiner*—Joseph W. Roskos
*Attorney, Agent, or Firm*—Cushman, Darby & Cushman

[57] ABSTRACT

An apparatus for detecting the gas-liquid ratio of a fluid including a gas-liquid separating chamber for separating a two-phase fluid into a gas component and liquid component, a first passage and a second passage through which the gas component and liquid component flow out from the separating chamber, respectively, and a detector for detecting when a gas-liquid ratio in the separating chamber reaches a predetermined value and for outputting a detection signal, a passage resistance ratio between the first and second passage being set so that the gas-liquid ratio in the separating chamber become the predetermined value when the gas-liquid ratio of the fluid reaches the detection target.

19 Claims, 3 Drawing Sheets

APPARATUS FOR DETECTING GAS-LIQUID RATIO OF A FLUID

BACKGROUND OF THE INVENTION

1. Field of the Invention

This invention relates to an apparatus for detecting a ratio of a gas component and liquid component (referred to as a gas-liquid ratio, hereafter) more particularly relates to an apparatus for detecting a gas-liquid ratio of two-phase fluid composed of gaseous phase and liquid phase which is sealed in a fluid conduit.

2. Description of the Related Art

As apparatus to detect a gas-liquid ratio, there is one which electrically measures the physical characteristics, such as the capacitance, of the two components.

Another apparatus, in which a gas-liquid ratio of a fluid can be detected with a device having a simple mechanism and at a low cost is known from Japanese Examined Patent Publication No. 61-14430.

In that, a receiver and an expansion valve are provided in a refrigeration system and connected to each other through a delivery conduit. Further, a chamber communicated to the delivery conduit is provided on an upper side of the center portion of the delivery conduit, and a means for detecting a condition of a cooling medium is provided in the chamber.

In the above apparatus, however, it is difficult to detect such a condition with a high accuracy because the cooling medium does not uniformly flow into the chamber from the delivery conduit. Especially, the apparatus has only one inflow-outflow port for the cooling medium. Further, the chamber is provided on an upper side of the delivery conduit, so the gas component of the fluid easily accumulated inside it. Accordingly, it does not efficiently work to detect a condition of shortage of the cooling medium in the refrigeration system, with high accuracy.

The object of the present invention is to provide an apparatus for detecting a gas-liquid ratio of a two-phase fluid composed of a gaseous phase and liquid phase with high accuracy.

Another object of the present invention is to provide an apparatus to detect a condition at which the gas-liquid ratio of a gas-liquid two-phase fluid reaches a predetermined target value to be detected, with a device having a simple mechanism and with high accuracy.

Still another object of the present invention is to provide an apparatus to detect variation of the gas-liquid ratio of a gas-liquid two-phase fluid with a device having a simple mechanism and with high accuracy.

Furthermore, another object of the present invention is to provide an apparatus to detect an increment of the gas component in a two-phase cooling medium composed of gaseous phase and liquid phase with a device having a simple mechanism and with high accuracy.

SUMMARY OF THE INVENTION

To attain the objects of the present invention, there is provided an apparatus for detecting a gas-liquid ratio of a fluid which comprises a gas-liquid separating chamber into which a gas-liquid two-phase fluid flows, which separates the fluid into a gas component and a liquid component, and which stores both of them therein, a first passage at an upper portion of the gas-liquid separating chamber through which one of the separated components flows out a second passage at a lower portion of the gas-liquid separating chamber through which the other separated component flows out.

A second passage at a lower portion of the gas-liquid separating chamber through which the other separated component flows out, and a means for detecting when a gas-liquid ratio in the gas-liquid separating chamber reaches a predetermined value and for outputting a detection signal, characterized in that a passage resistance ratio between the first and second passage is set so that the gas-liquid ratio in the separating chamber becomes the predetermined value when the gas-liquid ratio of the fluid reaches the detection target.

According to the present invention, each of the gas component and the liquid component stored in the gas-liquid separating chamber flows out from the chamber in accordance with a ratio defined by a passage resistance ratio between the first and second passages.

Therefore, when the amount of the gas component of a fluid flowing into the gas-liquid separating chamber increases, the amount of the gas component stored in the gas-liquid separating chamber also increases, conversely, when the amount of the liquid component of the fluid flowing into the gas-liquid separating chamber increases, the amount of the liquid component stored in the gas-liquid separating chamber also increases.

In the present invention, the passage resistance ratio between the first passage and the second passage is set in advance so that the gas-liquid ratio in the chamber reaches a predetermined value when the gas-liquid ratio of the fluid flowing into the gas-liquid separating chamber reaches a predetermined target value. The detecting means outputs a detection signal when the predetermined ratio is reached.

Thus, in the present invention, the time when the gas-liquid ratio of the fluid flowing into the gas-liquid separating chamber reached the target value can be accurately detected.

DESCRIPTION OF THE PREFERRED EMBODIMENTS

In the present invention, the apparatus is provided with a chamber separating a fluid into a gas component and a liquid component and with a passage for the outflow of the gas component and a liquid component.

A means is provided for detecting the level of a top surface of the liquid component contained in the gas-liquid separating chamber. The detecting means can also detect a variation of the gas-liquid ratio of the fluid, i.e., increment or decrement thereof, flowing into the chamber with respect to the ratio between the gas component and liquid component flowing out through the gas outflow passage and a liquid outflow passage, respectively.

A venturi is provided on a delivery conduit through which the gas-liquid two-phase cooling medium of a refrigeration cycle flows. A passage is diverged from the delivery conduit upstream of the venturi and communicated to the venturi. The gas-liquid separating chamber is provided on the divergent passage. A flow control means controls the ratio between the gas component and liquid component flowing out from the chamber.

Further, a detecting means is provided for detecting an increment of the gas component stored in the gas-liquid separating chamber to detect an increment of the gas component of the gas-liquid two-phase cooling medium.

In accordance with the construction of the apparatus, the cooling medium positively flows into the gas-liquid separating chamber from the delivery conduit under the influence of the venturi, and both the gas component and liquid component of the cooling medium are positively returned to the delivery conduit from the chamber.

In such a system as mentioned above, when the amount of the gas component of the cooling medium in the delivery conduit increases, the amount of the gas component of the medium flowing into the gas-liquid separating chamber exceeds the amount of the gas component flowing out from the chamber, whereby the amount of the gas component stored in the chamber is increased.

The increment of the gas component in the gas-liquid separating chamber is detected by the detecting means, whereby the increment of the gas component of the cooling medium, i.e., the decrement of the amount of the cooling medium in the refrigeration cycle, can be detected.

Examples of the present invention will now be described with reference to the attached drawings.

Figure 1:
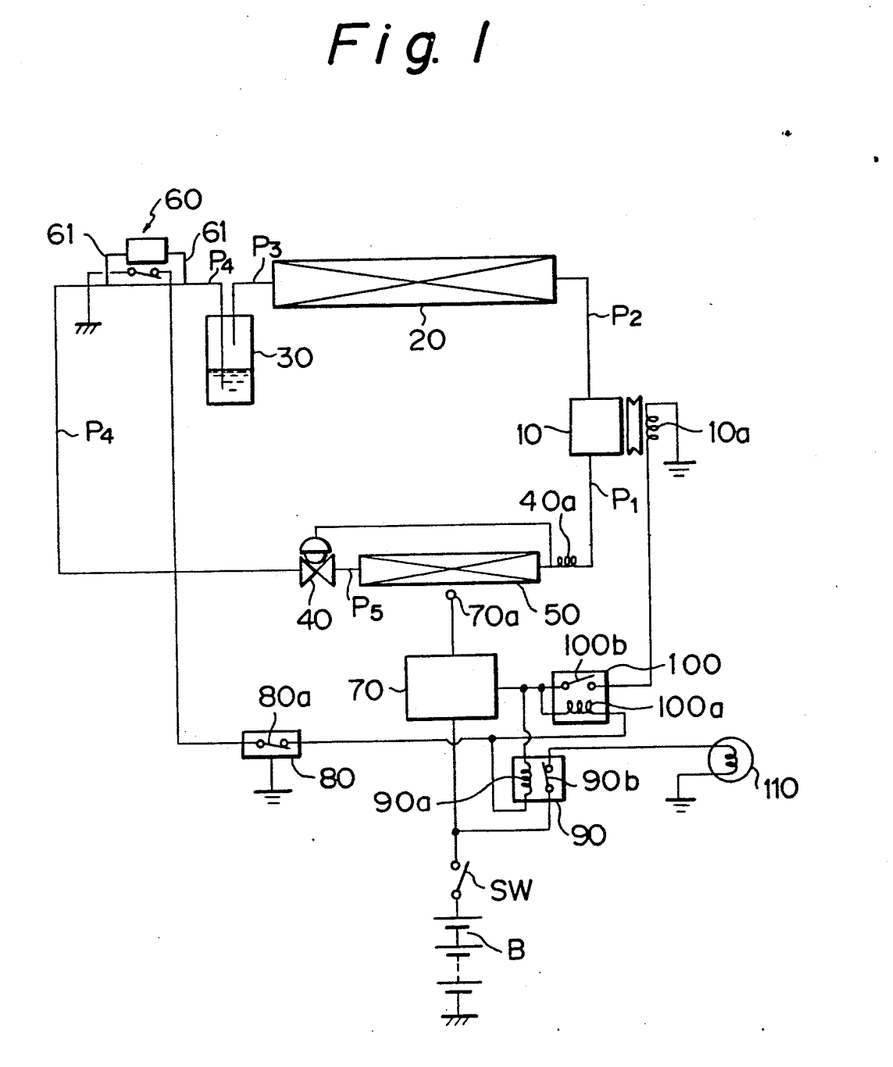
FIG. 1 is a block diagram of a refrigeration cycle of the present invention applied to an air-conditioner used in an automobile.

FIG. 1 shows an example of the present invention as applied to the refrigeration cycle of an air-conditioner for an automobile.

In the figure, the refrigeration cycle is provided with a compressor 10. The compressor 10 works by receiving driving power from an engine of the automobile under a selective connection in an electromagnetic clutch 10a to suck and compress the cooling medium flowing into it from a delivery conduit $P_1$ and to output it into a delivery conduit $P_2$ as a compressed cooling medium.

A condenser 20 is also provided for condensing the compressed cooling medium flowing into it under a heat radiating action of a cooling fan (not shown) and outputting the condensed cooling medium into a delivery conduit $P_3$.

A receiver 30 is provided for separating the condensed cooling medium into a gaseous phase cooling medium and a liquid phase cooling medium and for delivering only the liquid phase cooling medium into a delivery conduit $P_4$ as a circulating cooling medium.

An expansion valve 40 is provided for expanding the circulating cooling medium flowing into it through the delivery conduit $P_4$ in response to a detection signal of a thermo-sensitive element 40a provided on the delivery conduit $P_1$ with respect to the temperature of the cooling medium in the delivery conduit $P_1$ and for delivering the expanded cooling medium into an evaporator 50 through a delivery conduit $P_5$.

The evaporator 50 refrigerates air to be passed in to a cabin of an automobile and simultaneously delivers the expanded cooling medium flowing therein to the delivery conduit $P_1$.

Figure 2:
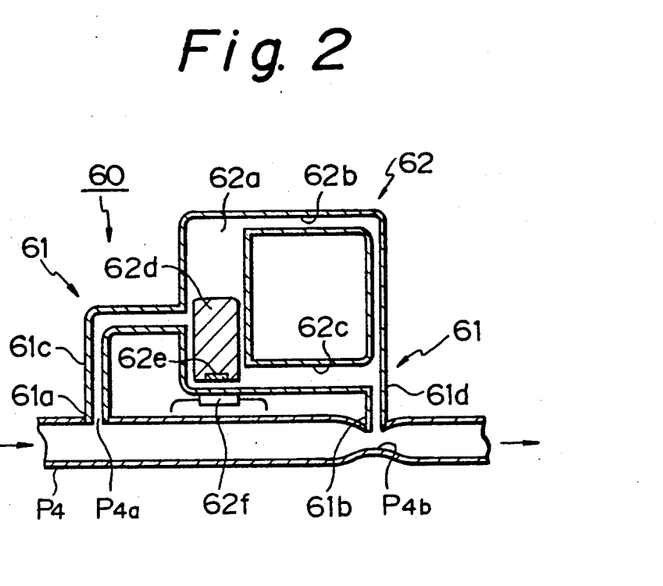
FIG. 2 is a cross-sectional view of an embodiment of a gas-liquid separating chamber used in the refrigeration cycle shown in FIG. 1.

The gas-liquid separating chamber 60, the main portion of the present invention, is provided as shown in FIG. 1. The gas-liquid separating chamber 60 is provided with a branch line 61, i.e., a bypassing conduit as shown in FIGS. 1 and 2. FIGS. 2 shows a view of gas-liquid separating chamber 60 from the reverse angle. As shown in FIG. 2, the branch line 61 is provided on a part of the delivery conduit $P_4$ so as to extend from an upper surface of the conduit $P_4$ into a space over the conduit $P_4$ to form a bypassing conduit.

More specifically, a venturi portion $P_{4b}$ is provided in a portion of the delivery conduit $P_4$. One end 61a of an upstream side of the branch line 61 is connected to a portion $P_{4a}$ of the delivery conduit $P_4$ located upstream of the venturi portion $P_{4a}$ and apart therefrom with a predetermined distance. The other end 61b of a downstream side of the branch line 61 is connected to the portion where the venturi portion $P_{4b}$ is formed.

In this construction, the amount of flow of the cooling medium diverged into the branch line 61 from the delivery conduit $P_4$ is set at a value sufficiently smaller than the amount of the flow in the delivery conduit $P_4$.

The gas-liquid ratio detecting chamber 60 is provided with a detecting means 62 for detecting the gas-liquid ratio of a fluid. The gas-liquid ratio detecting means 62 is mounted on an intermediate portion of the branch line 61.

The gas-liquid ratio detecting means 62 is provided with a gas-liquid separating chamber 62a, which chamber 62a is connected to an upstream portion 61c of the branch line 61 through a front wall of the chamber 62a and connected to a downstream portion 61d of the branch line 61 through a rear portion thereof.

In this construction, the gas-liquid separating chamber 62a sucks in the cooling medium flowing into the upstream portion 61c of the branch line 61 diverging from the delivery conduit $P_4$ by a sucking function caused by the venturi portion $P_{4b}$, separates the cooling medium thus introduced into a gaseous phase and a liquid phase, and stores them therein.

In this situation, the capacity of the gas-liquid separating chamber 62a is set at a small value so as to correspond to the amount of the diverged flow of the cooling medium introduced into the branch line 61.

On the other hand, the gas-liquid ratio detecting means 62 is provided with an upper side passage 62b and a lower side passage 62c. One end of the upper side passage 62b is connected to an opening provided on a top end of a rear wall of the gas-liquid separating chamber 62a, and the other end thereof connected to a portion in the vicinity of the downstream portion 61d of the branch line 61. One end of the lower side passage 62c is connected to an opening provided on a bottom end of a rear wall of the gas-liquid separating chamber 62a, and the other end thereof is connected to a portion in the vicinity of the downstream portion 61d of the branch line 61.

In this construction, if the passage resistance of the upper side passage 62b is r and that of the lower side passage 62c is R, the overall lengths and cross-sectional areas of the upper side passage 62b and the lower side passage 62c are set so as to make the passage resistance ratio $S = (r/R)$, for example, 0.75.

The reason why the passage resistance ratio $S=(r/R)$ is set at 0.75, for example, will be explained hereunder.

Figure 3:
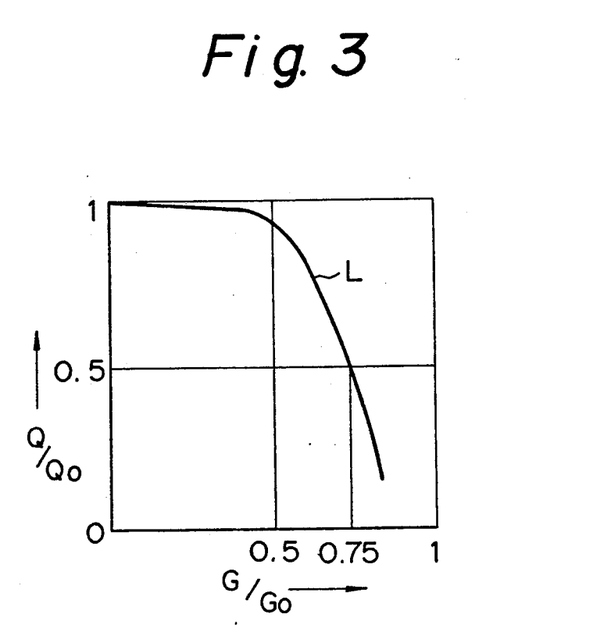
FIG. 3 is a graph of a relationship between a ratio of refrigerating performance and a gas-liquid condition in a gas-liquid separating chamber.

The rate of the refrigerating performance in a refrigeration cycle that is, the ratio of a current refrigerating performance in a refrigeration cycle Q to an initial refrigerating performance $Q_0$ ($Q/Q_0$), and the ratio of the amount of a gas component G contained in a cooling medium introduced into the gas-liquid separating chamber 62a to the total amount of the cooling medium $G_0$ ($G/G_0$) have the relationship as shown by a curve L shown in FIG. 3.

Note, that, Q shows the refrigerating performance at a certain instance in the working refrigeration cycle, and $Q_0$ shows the refrigerating performance of the refrigeration cycle at an initial time when a new refrigeration cycle has just been put into actual usage. The ratio of $Q/Q_0$ corresponds to the ratio of the amount of the gas component contained in the cooling medium flowing through the delivery conduit $P_4$ to the total amount of the cooling medium.

Accordingly, in order to properly detect a shortage of the refrigerating performance of the refrigeration cycle caused by leakage of the cooling medium from the delivery conduit system early in the refrigeration cycle, which leads to a shortage of lubrication for the compressor, it can be recognized that suitable values of the ratio of $Q/Q_0$ and the ratio of $G/G_0$, which can be determined by a pertinent point contained in the curve L, representing a reduction of the ratio of the refrigerating performance may be selected.

In this example, for example, when the ratio of t $Q/Q_0$ is approximately 0.5 ($Q/Q_0 \approx 0.5$), the reference value for detecting the insufficiency of the refrigerating performance is set at the ratio of $G/G_0 = 0.75$, and thereby the passage resistance ratio S is set at about 0.75 ($S \approx 0.75$) with respect to the ratio of $G/G_0 \approx 0.75$.

Thus, the gas component and the liquid component of the cooling medium flow out from the gas-liquid separating chamber 62a at a ratio corresponding to the value of $S \approx 60.75$.

Accordingly, when the gas-liquid ratio of the cooling medium flowing into the gas-liquid separating chamber 62a is equal to the ratio between the gas component flowing through the upper side passage 62b and the liquid component flowing through the lower side passage 62c (referred to as a gas-liquid ratio of outflow liquid), i.e., the ratio of $G/G_0$, is approximately 0.75 ($G/G_0 \approx 0.75$), it can be considered that the surface of the liquid stored in the gas-liquid separating chamber 62a is stable.

Accordingly, when a sufficient amount of the cooling medium is filled in the refrigeration cycle and the ratio of the refrigerating performance $Q/Q_0$ is more than 0.5, the gas-liquid ratio of the cooling medium flowing into the gas-liquid separating chamber 62a is less than the ratio between the gas component flowing through the upper side passage 62b and the liquid component flowing through the lower side passage 62c (referred to as a gas-liquid ratio of outflow cooling medium), i.e., the amount of the gas component of the cooling medium flowing into the gas-liquid separating chamber is less than the amount of the gas component of the cooling medium flowing out from the gas-liquid separating chamber 62a through the upper side passage 62b.

This contributes to make the ratio $G/G_0$ less than 0.75 ($G/G_0 < 0.75$), and holds the surface of the liquid in the gas-liquid separation chamber 62a at an upper level.

At that time, the liquid component of the cooling medium also flows out through the upper side passage 62b.

While, when the ratio of the refrigerating performance is below 0.5 ($Q/Q_0 < 0.5$), corresponding to the condition in which a sufficient amount of the cooling medium is not filled in the the refrigeration cycle, the gas-liquid ratio of the cooling medium flowing into the gas-liquid separating chamber 62a is more than the gas-liquid ratio of outflow cooling medium, i.e., the amount of the gas component of the cooling medium flowing into the gas-liquid separating chamber is more than the amount of the gas component of the cooling medium flowing out from the gas-liquid separating chamber 62a through the upper side passage 62b.

This contributes to make the ratio $G/G_0$ more than 0.75 ($G/G_0 > 0.75$), leading to a descent of the surface of the liquid in the gas-liquid separating chamber 62a. Ultimately, the gas component of the cooling medium also flows out through the lower side passage 62c.

A float 62d is movably provided inside of the gas-liquid separating chamber 62a along the longitudinal direction thereof. It is made of a foamed plastic material, for example, having a specific gravity lighter than the liquid component of the fluid contained in the gas-liquid separating chamber 62a while heavier than the gas component.

A plate 62e to be detected, made of a permanent magnet is attached to a bottom portion of the float 62d.

On the other hand, a normally closed type lead switch 62f is fixedly provided on an outer bottom surface of the gas-liquid separating chamber 62a at a position opposite to the plate 62e to be detected.

The lead switch 62f is actuated by magnetic detection of a position of the plate 62e when it is in a floating position in the liquid component which corresponds to the condition of $G > 0.75$ $G_0$.

The electrical circuit of the refrigeration cycle of the present invention will be explained with reference to FIG. 1.

A controller 70 is operated by electrical power supplied from a battery B through an operating switch SW which is in the ON condition. It energizes coils 90a and 100a of the relays 90 and 100, respectively, with the ON condition of a normally closed switch 80a of a delaying relay 80 in accordance with information detected by a thermo-sensitive sensor 70a with respect to an actual temperature in a cabin of an automobile, a predetermined temperature setting, and a temperature of air flowing out from an evaporator 50.

The delaying relay 80 enables energization of the coils 90a and 100a in an ON condition of the normally closed switch 80a when a lead switch 62f is in ON condition. When a predetermined time for example, 5 seconds, elapses after the lead switch 62f is turned off, the normally closed switch 80 is turned off to deenergize the coils 90a and 100a.

A relay 90 opens a normally opens closed switch 90b by energization of the coil 90a and turns off an alarm lamp 110 and vice versa.

A relay 100 closes a normally opened switch 100b by energization of the coil 100a and enables the controller 70 to control selective coupling of an electromagnetic clutch 10a and vice versa.

An operational switch SW is operated when an air-conditioner is to be operated.

In this example as explained above, the controller 70 starts to work when the engine of the automobile is operating and the operational switch SW is turned on to cool the cabin of the automobiles.

At this time, when a sufficient amount of the circulating cooling medium exists in the refrigeration cycle and simultaneously an amount of the liquid component of the cooling medium stored in the gas-liquid separating chamber 62a sufficiently exists, the float 62d is lifted up by the liquid component in the gas-liquid separating chamber 62a, and positioned at an upper portion of the chamber 62a, whereby the lead switch 62f is kept in the ON condition.

Therefore, the controller 70 energizes the coil 90a and 100a of relays 90 and 100, respectively, when the normally closed switch 80a in the delaying relay 80 is turned on.

Thus, the alarm lamp 110 is turned off due to the normally closed switch 90b being turned off along with the energization of the coil 90a.

When the clutch 10a is controlled by the controller 70 to couple the compressor with the engine due to the normally opened switch 100b being turned on by the energization of the coil 100a, the compressor 10 starts to operate by transmission of power from the engines, sucks the cooling medium in the delivery conduit $P_1$ therein, and compress the cooling medium thus sucked.

Then, the compressor delivers the compressed cooling medium into the delivery conduit $P_2$. After that, the condenser 20 receives the compressed cooling medium in the delivery conduit $P_2$, condenses it, and delivers the condensed cooling medium into the delivery conduit $P_3$.

Then, the receiver 30, receiving the condensed cooling medium in the delivery conduit $P_3$ with a lubricant oil therein, separates it into a liquid phase and a gaseous phase, and delivers the liquid phase into the delivery conduit $P_4$ with the lubricating oil as a circulating cooling medium.

The circulating cooling medium flowing into the delivery conduit $P_4$ is partly sucked and passed into the upstream portion of the branch line 61 under the venturi effect of the venturi portion $P_{4b}$ of the delivery conduit $P_4$.

The circulating cooling medium thus partially introduced into the upstream portion of the branch line 61 is separated into a gas component and liquid component in the gas-liquid separating chamber 62a.

Nevertheless, at this moment, since the amount of the cooling medium circulating in the refrigeration cycle is sufficient, as mentioned above, the inside of the gas-liquid separating chamber 62a is filled almost completely with the liquid component.

Accordingly, the float 62d is kept lifted up to an upper portion of the inside of the gas-liquid separating chamber 62a, so the liquid component stored inside the the branch line 61 through both the upper side passage 62b and the lower side passage 62c and then flows into the venturi portion $P_{4b}$ to converge with a main flow of the circulating cooling medium in the delivery conduit $P_4$.

On the other hand, the expansion valve 40 expands the circulating cooling medium received from the delivery conduit $P_4$ in accordance with a detection output of the thermo-sensitive element 40a and delivers the expanded cooling medium into the evaporator 50 with the lubricating oil through the delivery conduit $P_5$.

Therefore, the evaporator 50 cools the air flowing into the cabin of the automobile by the cooling medium flowing therein and returns the cooling medium to the delivery conduit $P_1$.

Thus, the air-conditioning inside the cabin of the automobile can be suitably controlled by the refrigeration performance of the evaporator 50 due to the sufficient amount of circulating cooling medium in the refrigeration cycle.

When this refrigeration cycle has been used for a long time, however, the cooling medium gradually leaks from the delivery conduit system in the refrigeration cycle, so the amount of the gaseous phase of the circulating cooling medium from the receiver 30 to the delivery conduit $P_4$ gradually increases.

Accordingly, the amount of the gas component separated from the fluid inside the gas-liquid separating chamber 62a is increased, while the amount of the liquid component thereof is decreased, whereby the surface of the liquid component drops and the float 62d descends.

When the gas component and the liquid component of the cooling medium flowing into the gas-liquid separating chamber 62a satisfy the condition of $G > 0.75\ G_0$, the gas component in the gas-liquid separating chamber 62a flows into the downstream portion of the branch line 61 not only through the upper side passage 62b but also through the lower side passage 62c.

At this moment, the float 62d takes a position corresponding to the condition of $G > 0.75\ G_0$, whereby the lead switch 62f is turned OFF by detection of the plate 62e.

After the lead switch 62f is turned off, when a predetermined delay time has passed, the delaying relay 80 turns off the normally closed switch 80a to demagnetize both coils 90a and 100a.

Accordingly, the relay 90 turns on the alarm lamp 110 by turning on the normally closed switch 90b by the coil 90a being demagnetized, while the relay 100 releases the electromagnetic clutch 10a and stops the operation of the compressor 10 by turning off the normally opened switch 100b by the coil 100a being demagnetized.

In this situation, for several seconds just after the refrigeration cycle starts to work, the float 62d may descend due to bubbles introduced into the cooling medium, but since the delaying relay 80 is provided, erroneous operation can be prevented in this refrigeration cycle.

As explained above, in repeated operation of the circulation of the cooling medium in the refrigeration cycle accompanying the operation of the compressor 10, the remaining amount of the cooling medium in the refrigeration cycle is reduced with the amount of the lubricating oil due to leakage of the cooling medium and the lubricating oil from the delivery conduit system in the refrigeration cycle. When the amounts of the gas component and the liquid component of the cooling medium flowing into the gas-liquid separating chamber 62a provided in the gas-liquid ratio detecting means 60 satisfy the condition of $G > 0.75\ G_0$ (refer to FIG. 3), the lead switch 62f detects the descended position of the float 62d by the plate 62e, turns on the alarm lamp 110, and simultaneously stops the operation of the compressor 10.

Accordingly, when the refrigeration performance ratio $(Q/Q_0)$ is reduced and satisfies the condition of $Q/Q_0 = 0.5$ (refer to FIG. 3), an alarm is provided to indicate the shortage of the cooling medium utilizing a mechanism having a simple and cheap construction. Further occurrence of malfunctions of the compressor caused by bad lubrication due to the resultant lack of the lubricating oil can be effectively prevented.

From these facts, it can be understood that the gas-liquid ratio detecting means 60 serves to detecting a shortage of the cooling medium.

The lubricating oil component is dissolved in the cooling medium, and circulated with it, but the amount thereof is about 2 to 3% and thus does not adversely affect the operation of the refrigeration cycle.

Further, in this example, the delaying relay 80 prevents erroneous operations which would occur in the circuit system from the time when the lead switch 62f is off to when both coils 90a and 100a are demagnetized.

A second example of the present invention, which is a modification of the first example as explained above, will be explained with reference to FIGS. 4 to 6.

Figure 4:
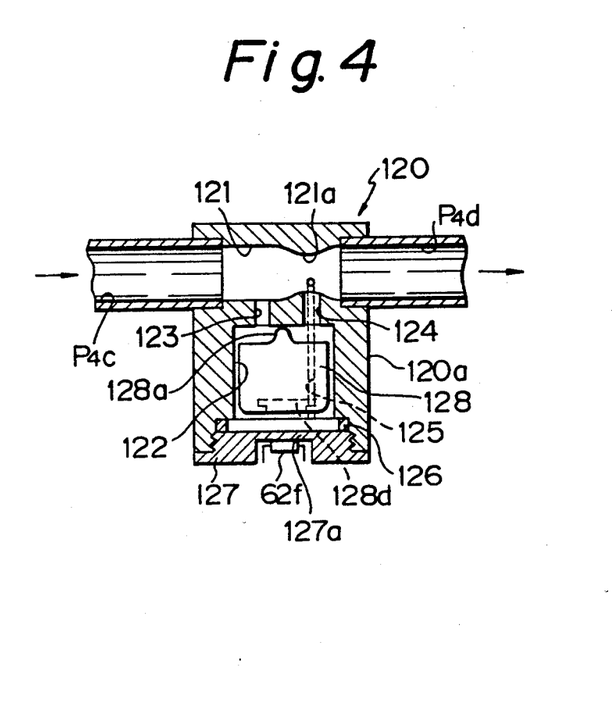
FIG. 4 is a cross-sectional view of another embodiment of a gas-liquid separating chamber of the present invention.

The technical feature of the second example is that a gas-liquid ratio detecting means 120 is adopted instead of the means 60. The gas-liquid ratio detecting means 120 is provided with a main body 120a hanging down under the delivery conduit $P_4$. Upper portions of both side walls of the main body 120a are connected to an end portion of the upstream side delivery conduit $P_{4c}$ and to an end portion of the downstream side delivery conduit $P_{4d}$ by soldering.

Note that the end portions of $P_{4c}$ and $P_{4d}$ are formed by taking off a certain intermediate portion of the delivery conduit $P_4$ therefrom.

In the upper portion of the main body 120a, a communicating passage 121 is provided, both ends thereof arranged at a position opposite to the end portion of the upstream side delivery conduit $P_{4c}$ and to an end portion of the downstream side delivery conduit $P_{4d}$ respectively. Further, a venturi portion 121a is provided at an intermediate portion of the communicating passage 121.

On the other hand, in the lower portion of the main body 120a, a cylindrical cavity 122 is provided having an opening facing downward and a step-like portion inside.

In a top wall portion of the small diameter cavity of the cylindrical cavity 122, a communicating passage 123 is provided to communicate the inside portion of the cylindrical cavity 122 having the step-like portion with an inside portion of the communicating passage 121 and especially with the portion located at an upstream side of the venturi portion 121a. A communicating passage 124 is also provided therein to communicate the inside portion of the cylindrical cavity 122 having the step-like portion with an inside portion of the venturi portion 121a.

Moreover, a communicating passage 125 is provided through the wall portion of the small diameter cavity of the cylindrical cavity 122 to communicate an inside of the large diameter cavity of the cylindrical cavity 122 with the inside of the venturi portion 121a.

In this example, the passage resistance ratio of the communicating passage 124 and the communicating passage 125 is set at the same value as defined by the passage resistance ratio of the upper side passage 62b and the lower side passage 62c as defined in the first example.

In the large diameter cavity of the cylindrical cavity 122, a cover 127 is provided fixedly fastened thereto by a screw thread or the like with an O-ring 126 therebetween to hermetically seal the inside of the cylindrical cavity 122.

Figure 6:
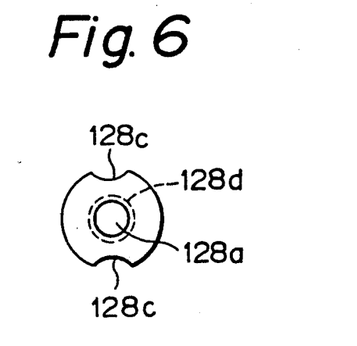
FIG. 6 is a plane view of a float used in the gas-liquid separating chamber shown in FIG. 4.

In the cylindrical cavity 122, a float 128 made of the same material as that of the float 62d in the first example is provided to freely move along the longitudinal direction of the cavity portion. A plate 128d made of a permanent magnet is provided on a bottom surface of the float 128.

Further, a projection 128a is provided on a top surface of the float 128 to ensure the existence of a gas-liquid separating chamber even when the float is raised completely. At least one grooved portion is provided on the outer surface of the side wall of the float 128 to keep communication with the communicating passage 125.

Figure 5:
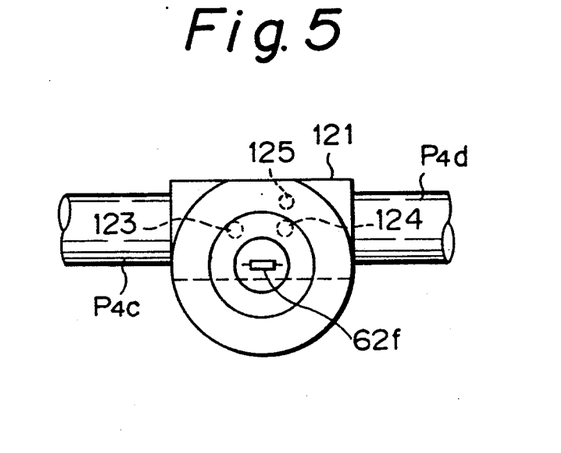
FIG. 5 is a bottom plane view of the gas-liquid separating chamber shown in FIG. 4.

On the other hand, a lead switch 62f is provided on an outer surface of a thin portion 127a formed at a center portion of the cover 127 opposite to and just below the portion of the bottom surface of the float 128 on which the plate 128d is provided.

Note that other elements of this example are similar to those used in the first example. That is, the venturi portion 121a, the smaller diameter cavity of the cylindrical cavity 122, the communicating passage 123, the communicating passage 124, the communicating passage 125, the float 128, and the plate 128d correspond to the venturi portion $P_{4b}$, the gas liquid separating chamber 62a, the branch line 61, the upper side passage 62b, the lower side passage 62c, the float 62d, and the plate 62e used in the first example respectively. The same operation and the same effect as obtained in the first example can be attained.

In the present invention, a thermistor which can change its internal resistance value in accordance with the amount of self heat radiation may be provided inside the gas-liquid separating chamber 62a (or inside the cylindrical cavity 122) instead of using the float 62d (or 128), the plate 62e (or 128a), and the lead switch 62f, and the normally closed switch 80a of the delaying relay 80 may be turned utilizing the resistance value corresponding to a heat capacity of the cooling medium when a sufficient amount of the gas component of the cooling medium exists in the gas-liquid separating chamber 62a to satisfy the condition of $G > 0.75\ G_0$.

In this situation, a means to detect the difference between an electric conductivity of the gas component and the liquid component may to used instead of the thermistor as above.

In these examples of the present invention, the pressure loss portion is not restricted only to the venturi portion $P_{4b}$ (or 121a). A suitable pressure loss portion having the same function as the venturi portion may be provided in the delivery conduit $P_4$ (or the communicating passage 121) instead of using the venturi portion.

Further, instead of using the venturi portion, another method in which a projection is projected into a fluid passage and the difference between a total pressure and a back pressure of the fluid is detected may be used.

Further, in the case of utilizing the venturi portion, a variable throttle valve may be provided at an intermediate portion of at least one of the upper side passage 62b (or the communicating passage 124) or the lower side passage 62c (or the communicating passage 125), whereby the detected value of the gas-liquid ratio may be changeable.

The present invention is not restricted to a refrigeration cycle for an air-conditioner and may of course be applied to a method for detecting a shortage of a cooling medium in any kind of refrigeration cycle and can also be generally applied to methods for detecting gas-liquid ratio of two-phase fluids.

We claim:

1. An apparatus for detecting a target value of a gas-liquid ratio of a fluid comprising:
   a gas-liquid separating chamber which separates a two-phase fluid consisting of a gaseous phase and liquid phase flowing therein into a gas component and a liquid component, and which stores both of said gas and liquid components therein;
   detecting means for detecting a ratio of said gas component and said liquid component in said gas-liquid separating chamber and for outputting a detection signal when said detected ratio reaches a predetermined value;
   a first passage through which one of said separated components in said gas-liquid separating chamber flows out of said gas-liquid separating chamber; and
   a second passage through which the other of said separated components in said gas-liquid separating chamber flows out of said gas-liquid separating chamber;
   wherein a passage resistance ratio between said first passage and said second passage is such that said predetermined value is detected by said detecting means when said gas-liquid ratio of said fluid reaches said target value.

2. An apparatus according to claim 1, further comprising a branch line, diverged from a main delivery conduit, which introduces part of said two-phase fluid into said gas-liquid separating chamber, and a pressure loss means, provided in said main delivery conduit which creates a low-pressure portion in said main delivery conduit having a pressure lower than that of a diverged portion where said branch line diverges from said main delivery conduit, which reduces a pressure of said fluid, said first and second passages connected to said low pressure portion of said main delivery conduit.

3. An apparatus according to claim 1, wherein said detecting means comprises a float having a specific gravity heavier than that of said gas component stored in said gas-liquid separating chamber and lighter than that of said liquid component thereof and a detector for detecting a position of said float.

4. An apparatus according to claim 1, wherein passage resistances of said first and second passages are determined by adjusting at least one of a passage length and a passage diameter of the passages.

5. An apparatus for detecting a gas-liquid ratio of a fluid, which comprises:
   a gas-liquid separating chamber into which a two-phase fluid consisting of a gaseous phase and liquid phase flows, which separates said fluid into a gas component and liquid component, and which stores both of them therein, a gas outflow passage out through which said gas component flows from said gas-liquid separating chamber at a first predetermined amount of flow, a liquid outflow passage out through which said liquid component flows from said gas-liquid separating chamber at a second predetermined amount of flow, and a detecting means for detecting a position of a surface of said liquid in said gas-liquid separating chamber, characterized in that said detecting means detects a variation of said gas-liquid ratio of said fluid flowing into said gas-liquid separating chamber with respect to a ratio defined by an amount of flow of gas in said gas outflow passage and an amount of flow of liquid in said liquid outflow passage by detecting a position of the surface of said fluid in said gas-liquid separating chamber.

6. An apparatus for detecting a gas-liquid ratio of a fluid according to claim 5, further comprising a branch line diverged from a main delivery conduit which introduces part of said two-phase fluid into said gas-liquid separating chamber, and a pressure loss means provided in said main delivery conduit which creates a low-pressure portion in said main delivery conduit having a pressure lower than that of a diverged portion where said branch line diverges from said main delivery conduit, which reduces a pressure of said fluid, said first and second passages connected to said low-pressure portion of said main delivery conduit.

7. An apparatus for detecting a gas-liquid ratio of a fluid according to claim 5, wherein said detecting means output a detecting signal when the surface of said liquid in said gas-liquid separating chamber falls below a predetermined value to enable detection of an increase of said gas to liquid ratio of said fluid.

8. An apparatus for detecting a gas-liquid ratio of a fluid according to claim 7, wherein said detecting means is further provided with means for outputting a signal indicating said increase of said gas to liquid ratio when said detecting signal is continuously output for a predetermined time.

9. An apparatus for detecting a gas-liquid ratio of a fluid according to claim 5, wherein said detecting means is further provided with a displaying means for displaying said increase of said gas to liquid ratio of said fluid when such condition is detected by said surface position of said liquid.

10. An apparatus for detecting a gas-liquid ratio of a fluid in which a delivery conduit is provided through which a two-phase cooling medium consisting of a gaseous phase and liquid phase used in a refrigeration cycle is circulated, comprising:
    a venturi provided in said delivery conduit,
    a branch line diverged from said delivery conduit at a position upstream of said venturi and connected to said venturi to separate a part of said cooling medium from said delivery conduit at said upstream portion while connected between a position downstream of said venturi and said delivery conduit to return said separated cooling medium from said venturi to said delivery conduit,
    a gas-liquid separating chamber provided in said branch line and separating said cooling medium into a gas component and a liquid component,
    a flow controlling means for controlling a ratio of a gas component to a liquid component flowing out from said gas-liquid separating chamber at a predetermined ratio and provided in said branch line and downstream of said gas-liquid separating chamber, and a detecting means for detecting an increase of said ratio of said gas component to said liquid component in said gas-liquid separating chamber and provided in said gas-liquid separating chamber.

11. An apparatus for detecting a gas-liquid ratio of a fluid according to claim 10, wherein said detecting means comprises a float having a specific gravity heavier than that of said gas component stored in said gas-liquid separating chamber and lighter than that of said liquid component thereof and a detector for detecting a position of said float.

12. An apparatus for detecting a gas-liquid ratio of a fluid according to claim 10, wherein said refrigeration cycle comprises a compressor and said apparatus further comprises a means for preventing operation of said compressor when said detecting means detects said increase of said ratio.

13. An apparatus for detecting a gas-liquid ratio of a fluid according to claim 10, wherein said apparatus further comprises a displaying means for displaying a lack of said cooling medium in said refrigeration cycle when said detecting means detects said increase of said ratio.

14. An apparatus for detecting a gas-liquid ratio of a fluid according to claim 10, wherein said apparatus further comprises an output means for outputting a signal indicating a lack of said cooling medium in said refrigeration cycle when said detecting means successively detects said increase of said ratio.

15. An apparatus for detecting a gas-liquid ratio of a fluid according to claim 10, wherein said apparatus is provided on an upper side of said delivery conduit.

16. An apparatus for detecting a gas-liquid ratio of a fluid according to claim 10, wherein said apparatus is provided hanging down beneath a lower side of said delivery conduit.

17. An apparatus for detecting a gas-liquid ratio of a fluid according to claim 10, wherein said branch line provided downstream of said gas-liquid separating chamber comprises a first passage connected to an upper portion of said gas-liquid separating chamber and a second passage connected to a lower portion of said gas-liquid separating chamber and said flow control means is provided in said first passage and said second passage respectively.

18. An apparatus for detecting a gas-liquid ratio of a fluid according to claim 17, wherein said flow control means controls each of the flows by adjusting passage resistances in both said first and second passages.

19. An apparatus for detecting a gas-liquid ratio of a fluid according to claim 10, wherein said apparatus comprises a main portion connecting an upstream portion of said delivery conduit and a downstream portion thereof and said main portion further comprising said venturi provided inside thereof, said gas-liquid separating chamber provided beneath said venturi of said main portion; an upstream side branch line connected between an upstream side of said venturi and said gas-liquid separating chamber provided in said main portion; and a downstream side branch line connected between said venturi and said gas-liquid separating chamber provided in said main portion, said downstream side branch line comprising a first passage connected between said venturi and said upper portion of said gas-liquid separating chamber and a second passage connected between said lower portion of said gas-liquid separating chamber and said venturi.

* * * * *